US008926676B2

(12) United States Patent  (10) Patent No.: US 8,926,676 B2
Pascual-Leone et al.  (45) Date of Patent: Jan. 6, 2015

(54) SYSTEMS AND METHODS FOR APPLYING SIGNALS, INCLUDING CONTRALESIONAL SIGNALS, TO NEURAL POPULATIONS

(75) Inventors: Alvaro Pascual-Leone, Wayland, MA (US); Bradford E. Gliner, Sammamish, WA (US); David Himes, Seattle, WA (US); Leif R. Sloan, Seattle, WA (US)

(73) Assignee: Advanced Neuromodulation Systems, Inc., Plano, TX (US)

( * ) Notice: Subject to any disclaimer, the term of this patent is extended or adjusted under 35 U.S.C. 154(b) by 816 days.

(21) Appl. No.: 11/697,696

(22) Filed: Apr. 6, 2007

(65) Prior Publication Data
US 2007/0288072 A1   Dec. 13, 2007

Related U.S. Application Data

(60) Provisional application No. 60/791,180, filed on Apr. 11, 2006.

(51) Int. Cl.
*A61N 1/36* (2006.01)
(52) U.S. Cl.
CPC ........ *A61N 1/36171* (2013.01); *A61N 1/36103* (2013.01); *A61N 1/3615* (2013.01); *A61N 1/36082* (2013.01)
USPC .................... 607/88; 607/45; 607/48; 606/41
(58) Field of Classification Search
CPC ....................................... A61N 1/0526–1/0539
USPC ..................................................... 607/45, 48
See application file for complete search history.

(56) References Cited

U.S. PATENT DOCUMENTS

| 2004/0073270 | A1* | 4/2004 | Firlik et al. ..................... 607/48 |
| 2004/0153129 | A1 | 8/2004 | Pless et al. |
| 2005/0021104 | A1 | 1/2005 | DiLorenzo |
| 2005/0021105 | A1 | 1/2005 | Firlik et al. |
| 2005/0070971 | A1* | 3/2005 | Fowler et al. .................. 607/45 |
| 2006/0015153 | A1 | 1/2006 | Gliner et al. |

OTHER PUBLICATIONS

Mansur C.G., "A Sham Stimulation Controlled Trial of rTMS of the Unaffected Hemisphere in Stroke Patients." *Neurology.* May 2005, 64(10):1802-1804; abstract, p. 1802 and 1804.
International Search Report for Application No. PCT/US2007/66213; Applicant: Northstar Neuroscience, Incorporated; Date of Mailing May 5, 2008 (2 pages).
European Patent Office, Supplementary European Search Report for EP 07760302 dated Nov. 23, 2012.

* cited by examiner

*Primary Examiner* — Lynsey Crandall

(57) ABSTRACT

Systems and methods for applying signals, including contralesional electromagnetic signals, to neural populations, are disclosed. A particular method can be directed to treating a patient having a subject neural population in a first (e.g., ipsilesional) hemisphere of the brain, with the subject neural population having, or previously having, a functionality capable of being improved. The method can include directing an application of electromagnetic signals at least proximate to a target neural population at a second (e.g., contralesional) hemisphere of the brain to at least constrain a functionality of the target neural population, which has transcallosal communication with the first hemisphere.

28 Claims, 11 Drawing Sheets

SYSTEMS AND METHODS FOR APPLYING SIGNALS, INCLUDING CONTRALESIONAL SIGNALS, TO NEURAL POPULATIONS

CROSS-REFERENCE TO RELATED APPLICATION

The present application claims priority to U.S. Provisional Application 60/791,180, filed Apr. 11, 2006 and incorporated herein by reference.

TECHNICAL FIELD

The present disclosure is directed generally toward systems and methods for applying signals to a patient, including electromagnetic signals, applied to a contralesional neural population. Such stimulation can be provided to a target neural population that is located at a region of the brain that is homologous or non-homologous relative to an affected neural population in the opposite brain hemisphere, and/or can be provided in accordance with a variety of other parameters.

BACKGROUND

A wide variety of mental and physical processes are controlled or influenced by neural activity in particular regions of the brain. In some areas of the brain, such as in the sensory or motor cortices, the organization of the brain resembles a map of the human body; this is referred to as the "somatotopic organization of the brain." Several areas of the brain appear to have distinct functions that are located in specific regions of the brain in most individuals. For example, areas of the occipital lobes relate to vision, regions of the left inferior frontal lobes relate to language in the majority of people, and particular regions of the cerebral cortex appear to be consistently involved with conscious awareness, memory, and intellect. This type of location-specific functional organization of the brain, in which discrete locations of the brain are statistically likely to control particular mental or physical functions in normal individuals, is herein referred to as the "functional organization of the brain."

Many problems or abnormalities with body functions can be caused by damage, disease and/or disorders of the brain. A stroke, for example, is one very common condition that damages the brain. Strokes are generally caused by emboli (e.g., vessel obstructions), hemorrhages (e.g., vessel ruptures), or thrombi (e.g., clotting) in the vascular system of a specific region of the cortex, which in turn generally causes a loss or impairment of a neural function (e.g., neural functions related to face muscles, limbs, speech, etc.). Stroke patients are typically treated using physical therapy to rehabilitate the loss of function of a limb or another affected body part. For most patients, little can be done to improve the function of the affected limb beyond the recovery that occurs naturally without intervention.

One existing physical therapy technique for treating stroke patients constrains or restrains the use of a working body part of the patient to force the patient to use the affected body part. For example, the loss of use of a limb is treated by restraining the other limb. Although this type of physical therapy has shown some experimental efficacy, it is expensive, time-consuming and little-used. Stroke patients can also be treated using physical therapy and/or drug therapies. For example, some types of drugs, including amphetamines, increase the activation of neurons in general. However, these drugs may have limited efficacy because the mechanisms by which they act are very non-selective, and because they cannot be delivered in appropriate concentrations directly at the site where they are needed. Still another approach is to apply electrical stimulation to the brain to promote the recovery of functionality lost as a result of a stroke. Typically, electrical stimulation is applied at or near the damaged tissue, or at homologous tissue located in the brain hemisphere opposite the hemisphere at which the neural damage has occurred (i.e., the contralesional hemisphere). While this approach has been generally effective, in some cases such stimulation may not improve functionality to the desired and/or expected degree. Therefore, there is a need to develop more effective and efficient treatments for rehabilitating stroke patients and patients who have other types of neurologic dysfunction or damage.

DETAILED DESCRIPTION

A. Introduction

Figure 1:
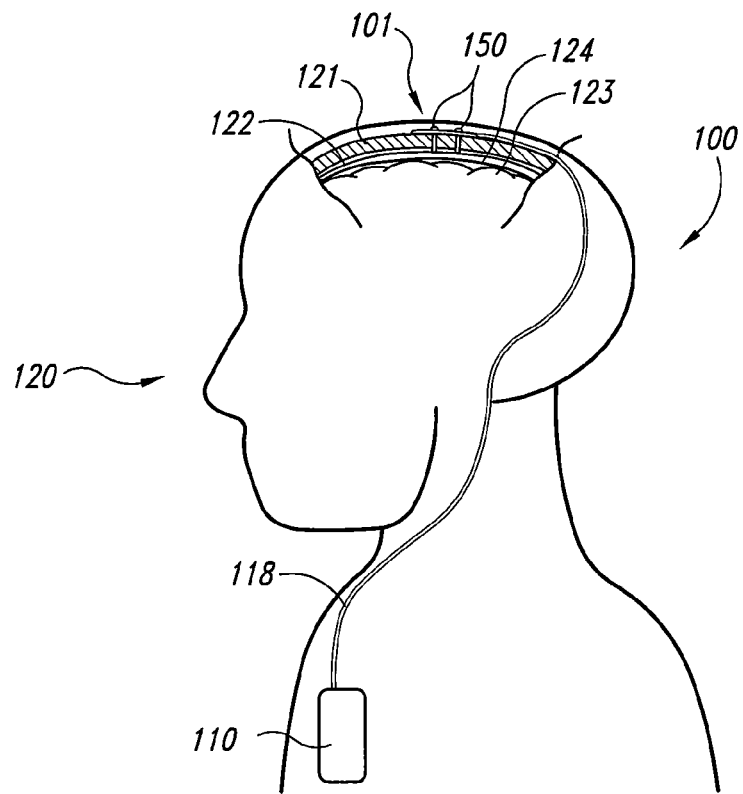
FIG. 1 is a partially schematic, left side illustration of a human brain and an implanted neurostimulation system positioned to provide electromagnetic signals in accordance with an embodiment of the invention.

The present disclosure describes (among other features), systems and methods for applying contralesional neural stimulation, e.g., stimulation applied to the brain hemisphere opposite the brain hemisphere at which neurological dysfunction or damage has occurred. In many instances, when a patient suffers from neurological damage or dysfunction in one brain hemisphere, the brain will naturally tend to activate or recruit neurons in the opposite hemisphere to compensate for or partially take over the functions previously performed by the damaged tissue. In some cases, the brain will tend to recruit tissue from contralesional homologous regions (e.g., those that control similar functions, but are located in the contralesional hemisphere), or non-homologous regions (e.g. contralesional regions that might otherwise control functions different than those performed by the damaged tissue). While this has been determined to provide a certain degree of functional recovery for the patient, it may have unintended consequences. For example, in some cases, it is believed that over-involvement of the contralesional tissue may discourage the body's natural efforts to recruit ipsilesional neural populations. Accordingly, in some instances, the ability of the brain to recover from neurological damage may be limited because the brain may tend not to recruit or sufficiently recruit the ipsilesional neural populations.

In light of the above, certain aspects of the invention are directed to a method for treating a patient having a subject neural population in a first (e.g., ipsilesional) hemisphere of the patient's brain, with the subject neural population having, or previously having, a functionality that is capable of being improved. The method can include directing an application of electromagnetic signals at least proximate to a target neural population at a second (e.g., contralesional) hemisphere of the brain to affect (e.g., constrain) a functionality of the target neural population, which may have transcallosal communication with the first hemisphere. For example, constraining the functionality of the target neural population can include depressing, inhibiting, and/or depotentiating the target neural population. It is believed that in at least some applications, constraining the functionality of the contralesional target neural population can result in increased functionality for ipsilesional neural populations. This effect can be further enhanced by providing facilitatory (rather than inhibitory) signals to the ipsilesional neural populations. In still further embodiments, the contralesional target neural population can additionally or alternatively receive facilitatory signals. For example, the contralesional target neural population can receive facilitatory signals after having received inhibitory signals (e.g., after the ipsilesional neural populations have undergone at least some functional recovery).

The parameters of the electromagnetic signals may be controlled or varied in order to obtain or enhance a particular type of effect. In particular embodiments, the frequency with which the electromagnetic signals are applied to the brain can be controlled to produce the constraining effect on the contralesional target neural population. For example, the signals can be applied at a frequency of from about 0.1 Hz to about 20 Hz. In more particular embodiments, the electromagnetic signals can be applied at a frequency of from about 1.0 Hz to about 10 Hz, or about 4 Hz to about 10 Hz. In some embodiments, the electromagnetic signals may be applied in an aperiodic or pseudorandom manner. The signals can be provided at less than a threshold level associated with the target neural population, at or approximately at a threshold level, and/or at greater than a threshold level, depending on factors that include the particular patient's condition. The target neural population can be homologous or non-homologous relative to the subject neural population.

The patient can also receive adjunctive therapy in addition to the electromagnetic signals. Adjunctive therapy can include physical therapy, cognitive therapy, drug-based therapy, and/or others. In particular embodiments, a characteristic of the electromagnetic signals can be based at least in part on a characteristic of the adjunctive therapy, and/or a characteristic of the adjunctive therapy can be based at least in part on a characteristic of the electromagnetic signals.

In further embodiments, electromagnetic signals can be delivered to the patient in other manners. For example, in some certain embodiments, facilitatory signals are provided to target populations in both hemispheres, whether or not constraining or inhibitory signals are provided to either hemisphere. The target population(s) in one hemisphere can be homologous or non-homologous with respect to a region of the brain in the other hemisphere that has a functionality capable of being improved. The target areas in each hemisphere can be homologous with respect to each other in some embodiments and non-homologous with respect to each other in other embodiments.

In still further embodiments, a variety of target site pairs or groups can be identified and, optionally, tested before selecting a at least one site pair or group that is expected to produce desired results. For example, during a first phase (e.g., a test phase), TMS or another non-invasive technique can be used to apply signals to a variety of site pairs, with one site of the pair in one hemisphere, and another site in the opposite hemisphere. In one embodiment directed toward facilitating motor function recovery or development, site pairs or groups may include, for example, neural sites selected from among portions of the primary motor cortex, the premotor cortex, the supplementary motor area (SMA), and/or the somatosensory cortex. In other embodiments, site pairs or groups may include other or additional neural areas, such as portions of the prefrontal cortex (PFC) or the auditory cortex. Several signal delivery parameters can be varied during the course of the test phase, including the signal delivery location, signal amplitude, whether the signal is facilitatory or inhibitory, and/or whether the locations are homologous or non-homologous, until the a desired result or outcome is produced. In at least one embodiment, the desired result can correspond to the a pair of sites that requires the lowest signal intensity to produce a desired motor given type of threshold response, such as a motor (e.g., motor evoked potential (MEP)), sensory, cognitive, emotional, or other response. Once this site pair is identified, one or more treatment signal delivery devices (e.g., implanted electrodes or other devices) can be positioned atrelative to the sites and used during a second phase (e.g., for therapeutic signal delivery). Optionally, the patient may undergo an adjunctive therapy during the second phase, but not the first phase.

In yet other embodiments, inhibitory and/or facilitatory electromagnetic signals can be delivered (sequentially or simultaneously) to target neural populations in the same hemisphere in a manner expected to enhance symptomatic benefit and/or facilitate functional development or restoration. Such target neural populations are generally functionally related or share at least some type of neural communication pathway. Various techniques or procedures described herein that are directed toward identifying target neural populations in different hemispheres may also be directed toward identifying target neural populations in the same hemisphere. As one example, inhibitory signals can be applied to at least a first target neural population that exhibits an abnormal activity level (e.g., a portion of the primary or secondary auditory cortex that is hyperactive due to an auditory dysfunction associated with tinnitus or auditory hallucinations), and facilitatory signals can be applied to at least a second target neural population (e.g., a different portion of the primary or secondary auditory cortex, and/or a portion of the secondary somatosensory cortex) in the same hemisphere, where the second target neural population is expected to have at least some capacity to contribute to a beneficial neuroplastic effect. Once established, a neuroplastic effect may last or persist on a long-term basis in the absence of extrinsic stimulation, or be sustainable with less frequent or less intense stimulation.

In the preceding example, the inhibitory signals can include anodal unipolar signals delivered at about 1-10 Hz, while the facilitatory signals can include cathodal unipolar signals delivered at about 50 or 100 Hz. In particular embodiments, the facilitatory signals can be applied at the same or a different intensity than the inhibitory signals. For example, if a symptomatically beneficial effect occurs in response to the application of the inhibitory signals at a peak current level $I_1$, then the facilitatory signals can be applied at an intensity or peak current level $I_2$ that is approximately 20%-80% (e.g., about 25%-75%, or about 50%) of $I_1$. Depending upon embodiment details, the facilitatory signals may be applied during a behavioral therapy session (e.g., an auditory discrimination training session). During the behavioral therapy session, the inhibitory signals may be applied at a reduced intensity or interrupted, depending upon short-term or long-term patient progress. Outside of a behavioral therapy session, the facilitatory signals may be applied at a reduced intensity or not at all.

Further embodiments of the invention are directed to computer-readable media for treating neurological dysfunctions. Such media can include a detection component configured to receive an indication of a change in functionality of a subject neural population of a patient's brain, with the subject neural population having a functionality that is capable of being improved. The media can include a direction component configured to direct a change in an electromagnetic signal applied to the patient's brain, possibly based at least in part on the indication received by the detection component. The change in the signal can include a change from an inhibitory signal to a facilitatory signal. In other embodiments, the direction for a change from an inhibitory signal to excitatory signal can be based upon a timing component (e.g., instead of a detection component) that includes information corresponding to expected times at which a change in electromagnetic signal is expected to increase functionality of a subject neural population of a patient's brain.

B. Systems and Methods for Providing Electromagnetic Signals

FIG. 1 is a schematic illustration of a representative signal delivery system 100 implanted in a patient 120 to provide electromagnetic signals in accordance with several embodiments of the invention. The signals can be directed to tissue to change (e.g., inhibit and/or facilitate) the functionality level of the tissue. The system 100 can include at least one signal delivery device 101, e.g., an electrode device carrying one or more electrodes 150. The signal delivery device 101 can be positioned in the skull 121 of the patient 120, with the electrodes 150 positioned to deliver electrical signals to target areas of the brain 123. For example, the electrodes 150 can be positioned just outside the dura mater 122 (which surrounds the brain 123) to affect cortical tissue. In other embodiments described later with reference to FIGS. 9 and 10, the electrodes 150 can penetrate the dura mater 122 to affect subcortical tissues. In still further embodiments, the electrodes 150 can penetrate the dura mater 122 but not the underlying pia mater 124, and can accordingly provide electromagnetic signals through the pia mater 124. In yet further embodiments, the signal delivery device 101 can include other devices, e.g., TMS devices or tDCS devices.

The signal delivery device 101 can be coupled to a pulse system 110 with a communication link 118. The communication link 118 can include one or more leads, depending upon the number and arrangement of electrodes 150 carried by the signal delivery device 101. The pulse system 110 can direct electromagnetic signals to the signal delivery device 101 to affect target neural tissues (e.g., in an inhibitory and/or facilitatory manner). Several embodiments for selecting the target neural tissues and providing signals to the target neural tissues as part of a treatment regimen are described below. In other embodiments, the signal delivery system 100 may comprise one or more microstimulators (e.g., a BION™ (Advanced Bionics Corp., Sylmar, Calif.)) implanted relative to a set of target neural populations in one or both brain hemispheres.

Figure 2:
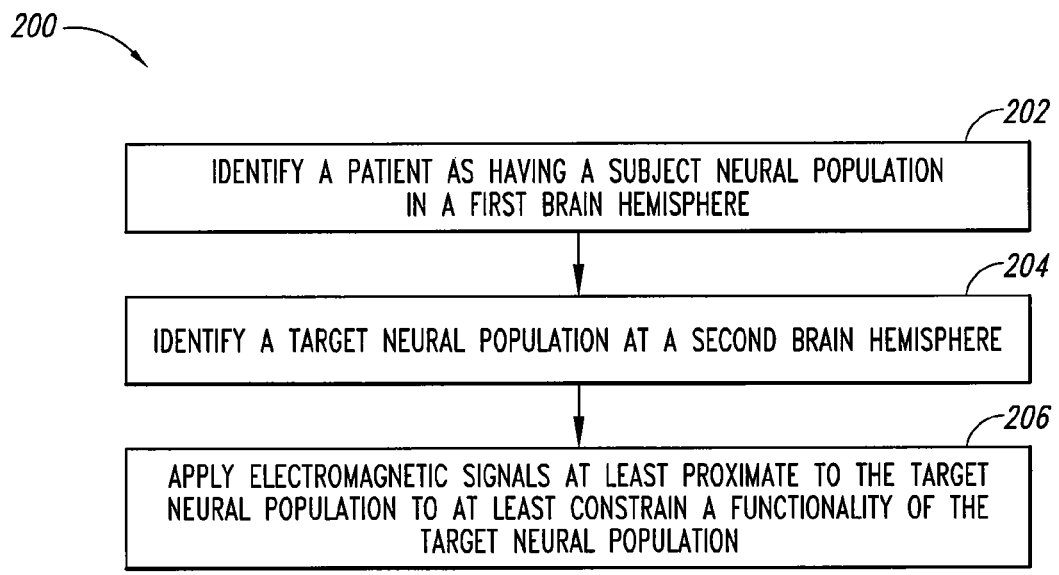
FIG. 2 is a flow diagram illustrating aspects of a process for treating a patient in accordance with an embodiment of the invention.

FIG. 2 is a flow diagram illustrating a process 200 for treating a patient. The process 200 can include identifying a patient as having a subject neural population in a first hemisphere of the patent's brain (process portion 202). The subject neural population can include an affected neural population that has a reduced (or non-existent) level of functionality, for example, as a result of a stroke or other event. In other embodiments, the subject neural population may have a normal functional level. In either embodiment, it may be desirable to enhance and/or improve the level of functionality that is (or was) provided by the subject neural population. In many instances, it will be a neural population other than the subject neural population that provides the enhanced and/or improved functionality. Many of the embodiments described below are described in the context of affected neural populations, e.g., ipsilesional populations; however in many instances, the techniques described in the context of these embodiments can be applied in the context of other subject neural populations as well (e.g., "normal" neural populations, or other neural populations that already provide functionality at normal or better levels). Accordingly, these techniques can be applied in the context of a variety of subject neural populations that have (or had) a functionality level that is capable of being improved.

The process 200 can further include identifying a target neural population at a second (i.e., opposite) hemisphere of the patient's brain (process portion 204). Any of several techniques can be used to identify and/or locate the subject neural population and the target neural population. Representative techniques include locating the populations via anatomical landmarks (e.g., brain structures that are located relative to the populations in a manner that is consistent from one patient to the next). Anatomical imaging (e.g., magnetic resonance imaging or MRI) techniques may also be used. In further embodiments, other techniques, including functional imaging, metabolic imaging and/or anatomical spectroscopy can be used to locate the neural populations. Techniques such as EEG may also be employed. In a particular embodiment, a different technique can be used to locate the subject neural population than is used to locate the target neural population. For example, functional MRI (fMRI) techniques can be used to locate the subject neural population (which may be damaged), and anatomical landmarks can be used to locate the target neural populations (which may be undamaged or less damaged). In other embodiments, other techniques and/or combinations of techniques can be used to locate the neural populations. For example, diffusion tensor imaging (DTI) techniques can be used to identify viable neural tracts, which can in turn be used to identify target neural populations. In a particular example, the target neural population(s) may be selected based at least in part on an indication of robust or damaged neural tracts associated with the population(s).

In process portion 206, the method can include applying electromagnetic signals at least proximate to the target neural population to at least constrain a functionality of the target neural population from increasing, expanding and/or otherwise becoming enhanced. For example, the electromagnetic signals can be applied to the target neural population to depress, depotentiate, disrupt, and/or otherwise inhibit the neural population from assuming functions normally performed by the subject neural population. For purposes of conciseness, signals that at least constrain the functionality of a target neural population are referred to herein as inhibitory signals.

In particular embodiments, delivering inhibitory signals to a contralesional target neural population can allow neural populations in the ipsilesional hemisphere of the patient's brain to assume a role that enhances particular or overall functionality of the brain. It is believed that, in at least some instances, the ipsilesional population(s) may not exhibit improved functionality (or may exhibit a reduced level of improvement) in the absence of constraining the contralesional population(s), because the contralesional neural population(s) achieve improvements instead. It is further believed that, in at least some cases, increased functionality of the ipsilesional tissue, alone or in combination with increased functionality of the contralesional tissue, may provide an overall increased level of functionality when compared with improvements in contralesional functionality alone.

Figure 3:
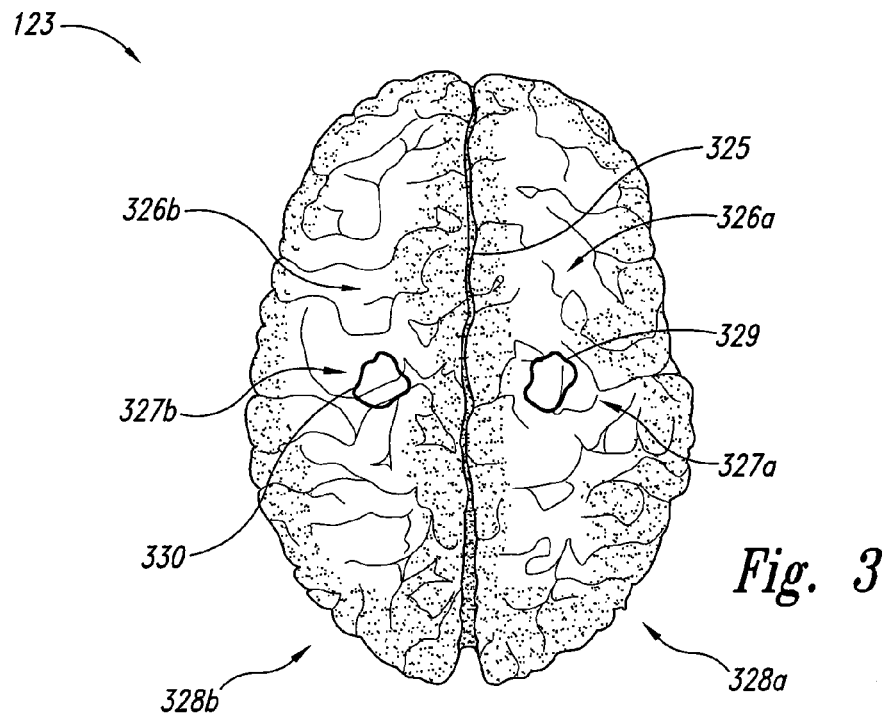
FIG. 3 is a top view of a patient's brain illustrating an affected neural population and a target neural population located contralesionally at an homologous brain structure.
Figure 4:
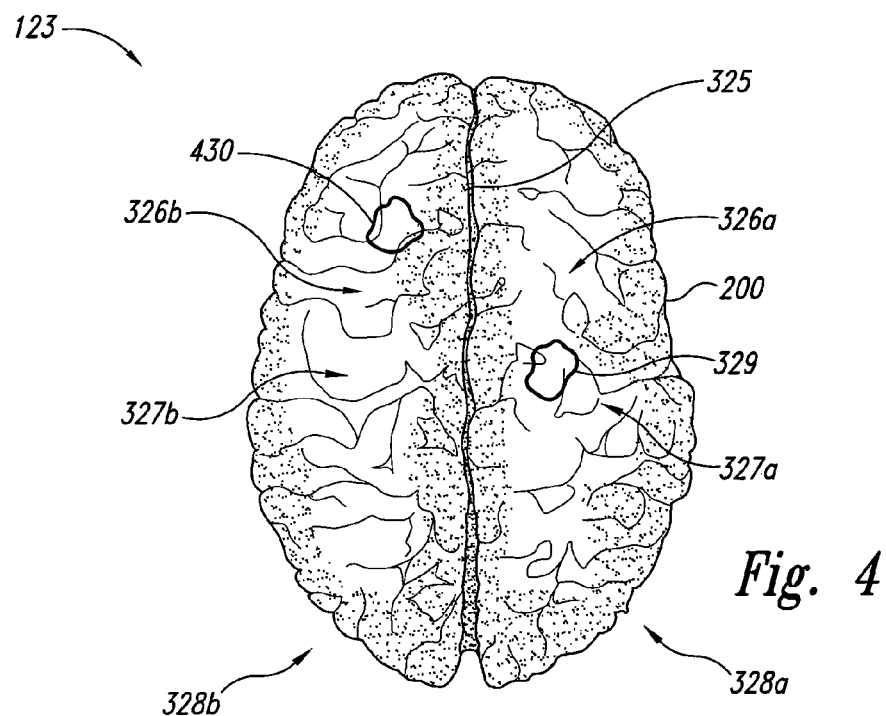
FIG. 4 illustrates a top view of the brain in which a contralesional target neural population is located at a region that is non-homologous relative to the affected neural population.

FIGS. 3 and 4 illustrate human brains with representative affected neural populations and target neural populations located in accordance with embodiments of the invention. Beginning with FIG. 3, the brain 123 includes the right hemisphere 328a and the left hemisphere 328b, with the corpus callosum 325 positioned between the two hemispheres to provide for interhemispheric communication. The right hemisphere 328a includes many functionally delineated structures. For purposes of illustration, the right premotor cortex 326a and the right primary motor cortex 327a are specifically identified in FIG. 3 and described below; however it will be understood by those of ordinary skill in the relevant art that the techniques described herein may be applied to other brain structures (for example, portions of the SMA (e.g., the pre-SMA), the primary and/or secondary somatosensory cortex, the primary and/or secondary auditory cortex, or the PFC (e.g., the dorsolateral PFC)) as well. The left hemisphere 328b includes homologous structures, e.g., the left premotor cortex 326b and the left primary motor cortex 327b.

In a particular aspect of an embodiment shown in FIG. 3, the patient can have a subject neural population 329 located at the right hemisphere 328a. As used herein, the term "subject neural population" refers generally to a neural population having a level of functionality that can be improved, whether its current functional level is normal or not. In a particular example, the subject neural population 329 can be located at the right primary motor cortex 327a. Accordingly, the patient may suffer a reduction and/or other dysfunction of his or her motor capabilities. The subject neural population 329 can be affected by any of a variety of damaging conditions or events, including a stroke, brain trauma, brain disease (e.g., Parkinson's disease or Alzheimer's disease), and/or other ischemic or non-ischemic events. In other embodiments, the subject neural population can have a normal functioning level, but nonetheless, a level that can be improved.

The practitioner can select a target neural population 330 that is contralesional (e.g., at the left hemisphere 328b) and, in this instance, homologous (e.g., at the left primary motor cortex 327b). When inhibitory electromagnetic signals are applied to the target neural population 330, the target neural population 330 can be constrained from taking on functions associated with the subject neural population 329, which, in the absence of inhibitory electromagnetic signals, it might otherwise take on. It is expected that, in at least some embodiments, the result of inhibiting the target neural population 330 is that the subject neural population 329 and/or tissues proximate to the subject neural population 329 will be more likely to assume functions that may have been lost when the subject neural population 329 was damaged.

In some instances, the level of functionality regained by the patient at sites other than the target neural population 330 (e.g., at sites at or proximate to the subject neural population 329) may be less than a level corresponding to a full and/or expected level of recovery overall, and/or may be less than a level of recovery that would be associated with the target neural population 330 were it not inhibited. In such instances, the practitioner can follow inhibitory electromagnetic signals directed to the target neural population 330 with facilitatory (e.g., excitatory) electromagnetic signals, also directed to the target neural population 330. In some cases, the difference between inhibitory and facilitatory signals can be controlled by controlling signal delivery parameters, for example, the frequency (or other waveform parameters) via which electromagnetic signals are delivered to the patient. Accordingly, the practitioner can switch from inhibitory to facilitatory signals without moving the corresponding signal delivery device(s) (e.g., without moving the electrode(s) that deliver the signals, and without implanting a new electrode). The overall benefit to the patient may be increased relative to some conventional techniques because the functionality of the patient's brain 123 may be enhanced both ipsilesionally and contralesionally. In particular, by deferring contralesional facilitatory signals, the ipsilesional hemisphere may be forced to take on functions that otherwise might be assumed, at least in part, by the contralesional hemisphere. The contralesional hemisphere can then take on additional functions (with aid from facilitatory electromagnetic signals) to supplement the increased functionality of the ipsilesional hemisphere.

To further encourage recovery at the ipsilesional hemisphere (e.g., the right hemisphere 328a), the practitioner may apply facilitatory electromagnetic signals to selected populations of the right hemisphere 328a. Such populations may be located at or adjacent to the subject neural population 329, and/or at other locations of the right hemisphere 328a that are expected to or are likely to assume such functions. In a particular aspect of this embodiment, the ipsilesional hemisphere can receive facilitatory signals at the same time the contralesional hemisphere receives inhibitory signals. As described above, the contralesional hemisphere (e.g., the left hemisphere 328b) can subsequently receive facilitatory signals (e.g., at the target neural population 330), for example, after enough time has lapsed that such stimulation will not discourage an increase in functionality at the (ipsilesional) right hemisphere 328a.

In some cases, the contralesional target neural population that would normally assume some or all functions of the subject ipsilesional neural population may not be located at a structure that is homologous to the subject neural population. For example, referring now to FIG. 4, the patient may have a subject neural population 329 located at the left primary motor cortex 327a, and a contralesional neural population expected and/or targeted to affect or assume at least some of the function of the subject neural population 329 may be located at the non-homologous left premotor cortex 326b. Accordingly, a target neural population 430 can be located at the left premotor cortex 326b. The target neural population 430 can (at least initially) be constrained or inhibited, as described above, during which time the patient's brain 123 can increase functionality of neural populations located at the right hemisphere 328a. Signals may also be applied to multiple target populations within the same brain hemisphere.

For example, inhibitory (and, optionally, subsequent facilitatory) signals may be applied to both homologous and non-homologous contralesional populations. In some cases the (non-homologous) target neural population 430 may have more transcallosal communication with the right hemisphere 328a than does the homologous neural population. Accordingly, the non-homologous target neural population 430 may, in the absence of inhibitory signals, be at least as likely to assume functions carried out by the affected neural population. Therefore, inhibiting the non-homologous population, at least initially, may provide for enhanced ipsilesional functioning.

Figure 5:
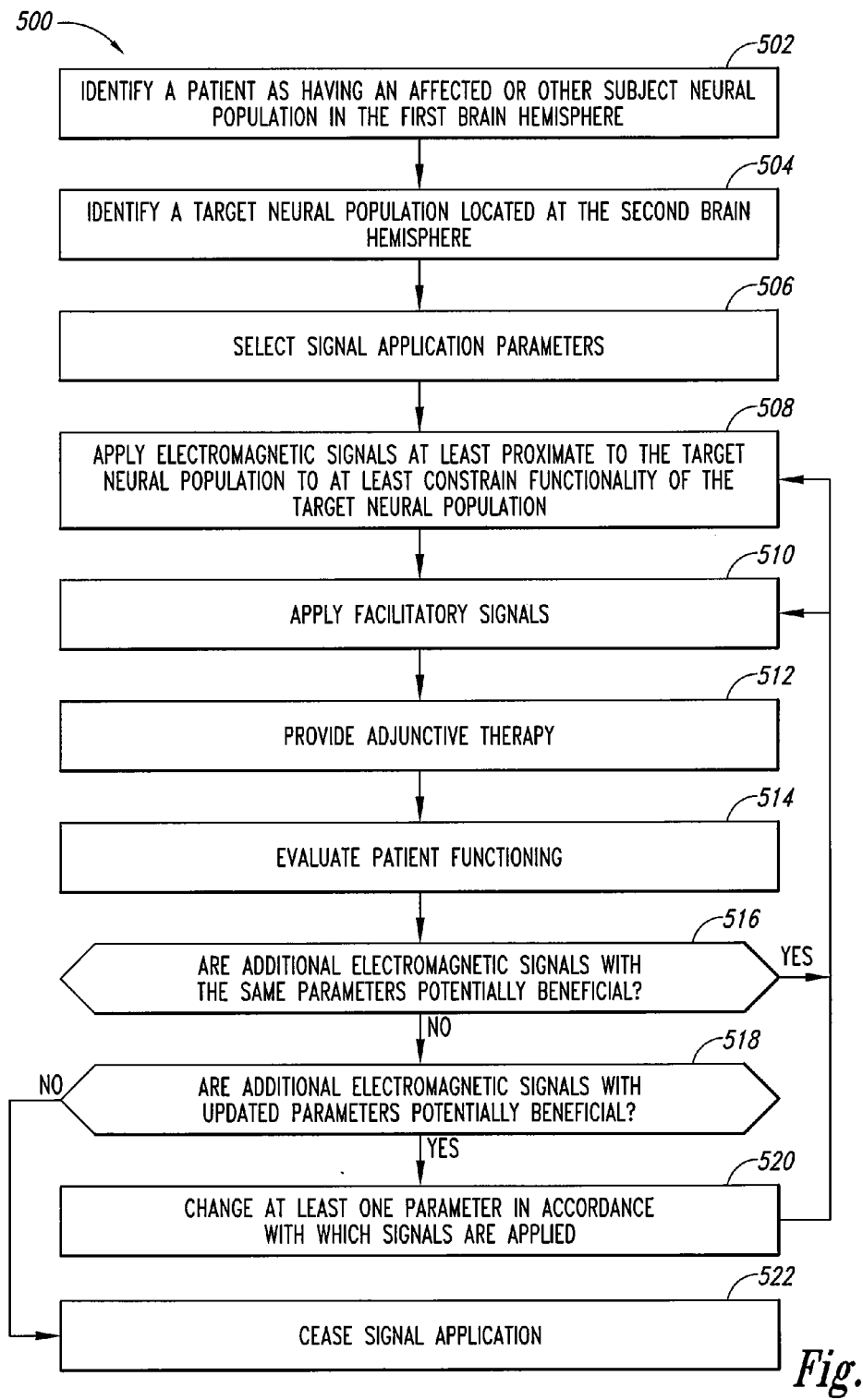
FIG. 5 is a flow diagram illustrating a process for treating a patient in accordance with another embodiment of the invention.

FIG. 5 illustrates a process 500 for treating a patient in accordance with another embodiment of the invention, and reflects several of the steps described above with reference to FIGS. 3 and 4. The process 500 can include identifying a patient as having an affected (or other subject) neural population in a first hemisphere (process portion 502) and identifying a target neural population at a site located at a second hemisphere (process portion 504). Process portion 506 can include selecting parameters in accordance with which electromagnetic signals are to be applied to the target neural population. These parameters can include waveform parameters, for example, the amplitude (current and/or voltage), frequency, pulse width, and/or interpulse interval of the signals. The signals can be applied in bursts (e.g., at theta-burst frequencies and/or other frequencies corresponding to naturally occurring alpha, beta, gamma, or delta frequency ranges), and the frequency of the signals can be varied in a random, pseudorandom, chaotic and/or other aperiodic fashion to achieve a desired neurologic result (e.g., at least constrain a type of neural function) or at least reduce the likelihood for neural adaptation or habituation. These and other representative examples are described in U.S. Published Application No. US2006/0015153A1, incorporated herein by reference.

In particular embodiments, the frequency can be selected to be from about 0.1 Hz to about 20 Hz (or, in a further particular embodiment, from about 1.0 Hz to about 10 Hz) to at least constrain neural functionality. The amplitude (current and/or voltage) of the signal can be selected to have a desired relationship relative to the threshold level for the target neural population (e.g., the level at which the target neural population generates an action potential). For example, in particular embodiments, the amplitude of the signal can be from about 5-10% to about 90-95% of the threshold level. In further embodiments, the signal amplitude can be 80% or less of the threshold level, and in other embodiments, 80% or more of the threshold level. Certain embodiments may use suprathreshold signal amplitudes at one or more times. Any or all of the foregoing parameters can be selected to inhibit the target neural population from assuming neural functions (e.g., neural functions formerly performed by the affected neural population). Accordingly, when in process portion 508 the electromagnetic signals are applied at least proximate to the target neural population, the signals can at least constrain the functionality of the target neural population.

In process portion 510, facilitatory electromagnetic signals can optionally be applied to the patient, for example, contralesionally at the target neural population (e.g., after the inhibitory stimulation routine has been completed). Facilitatory signals can also be optionally applied ipsilesionally (e.g. at least proximate to the affected neural population, and/or another suitable ipsilesional population). For example, facilitatory stimulation can be applied to the affected neural population, or to a region proximate to the affected neural population, or to an ipsilesional and/or contralesional region in association with inhibitory stimulation being applied to the target neural population. The two types of stimulation can be applied simultaneously to the different neural populations in some embodiments, and can be applied sequentially in other embodiments.

The signals provided in process portion 508 and/or process portion 510 can be provided in association with other types of treatment, including non-electromagnetic treatment techniques and/or facilitatory electromagnetic signals. For example, in process portion 512, the process 500 can include providing one or more additional therapies, e.g., chemical stimulation, behavioral therapy, and/or other types of adjunctive therapy before, during, and/or after the application of electromagnetic signals. Suitable chemical agents can include norepinephrine and/or an adenosine A1 receptor antagonist, or Botox (e.g., to reduce patient symptoms associated with spasticity). Suitable behavioral therapies can include physical therapy activities, movement and/or balance exercises, activities of daily living (ADL), vision exercises, reading exercises, speech tasks, memory or concentration tasks, visualization or imagination exercises, auditory activities, olfactory activities, relaxation activities, cognitive skills training or practice, comprehension tasks, and/or other types of behaviors, tasks or activities.

The particular adjunctive therapy selected to be performed in process portion 512 can be based upon the particular condition of the patient and/or the neural dysfunction from which the patient suffers. For example, if the patient suffers from a motor dysfunction, the adjunctive therapy can include a motor task. If the patient suffers from a cognitive dysfunction or a language dysfunction, the adjunctive therapy can include a cognitive task or a language-based task, respectively. In any of these embodiments, the relative timing between the application of electromagnetic signals and the adjunctive therapy portion of the treatment regimen can be controlled and/or altered during the course of the treatment regimen, and can be simultaneous and/or sequential during various phases of the treatment regimen.

Process portion 514 includes evaluating the functioning level of the patient. For example, process portion 514 can include having the patient engage in a test of the patient's neural functioning level, with the test selected based upon the function expected to show improvement. For example, if the patient has been treated for a motor dysfunction, process portion 514 can include evaluation of a motor task performed by the patient. If the patient suffers from a language or cognitive dysfunction, process portion 514 can include an appropriate language-based or cognitive task, respectively.

Based upon the performance evaluation conducted in process portion 514, process portion 516 can include determining whether delivery of additional electromagnetic signals with the same parameters is potentially beneficial. If so, the process returns to process portion 508 for delivery of additional electromagnetic signals. If not, then in process portion 518, it is determined whether additional electromagnetic signals with updated (e.g., different) parameters are potentially beneficial. If so, process portion 520 can include changing at least one parameter in accordance with which electromagnetic signals are applied to the patient. For example, process portion 520 can include changing a location at which signals are applied, changing from inhibitory to facilitatory signals, and/or changing a waveform characteristic of the signals. The process then returns to process portion 508 (and/or process portion 510) for delivery of additional signals in accordance with the new parameters. If additional signals with updated parameters are not expected to provide further benefit, then signal delivery ceases in process portion 522.

C. Further Methods for Applying Electromagnetic Signals

Figure 6A:
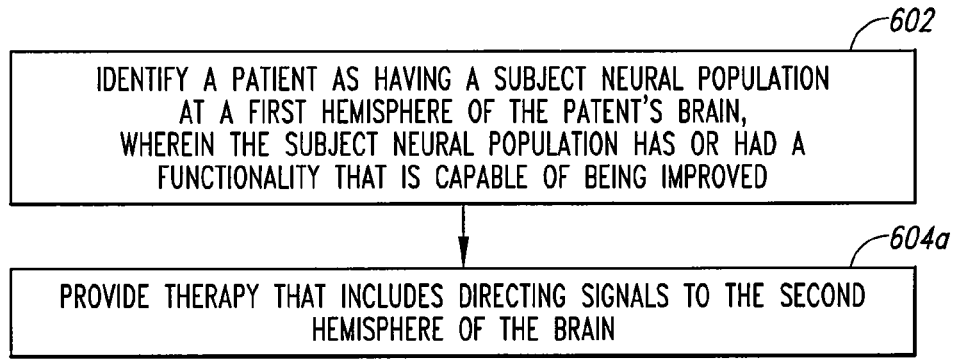
FIGS. 6A-6N are flow diagrams illustrating processes for treating patients in accordance with still further embodiments of the invention.
Figure 6B:
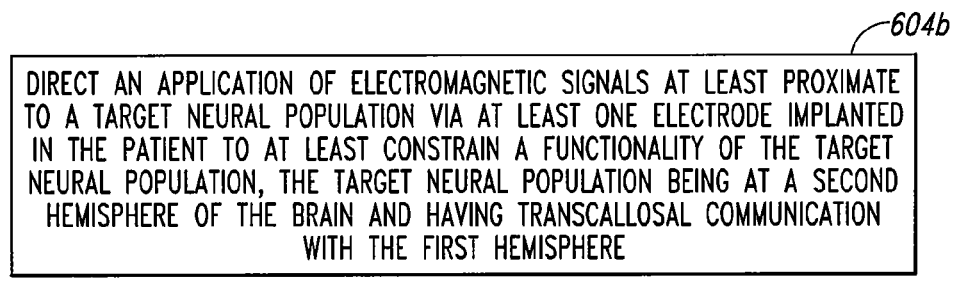
Figure 6C:
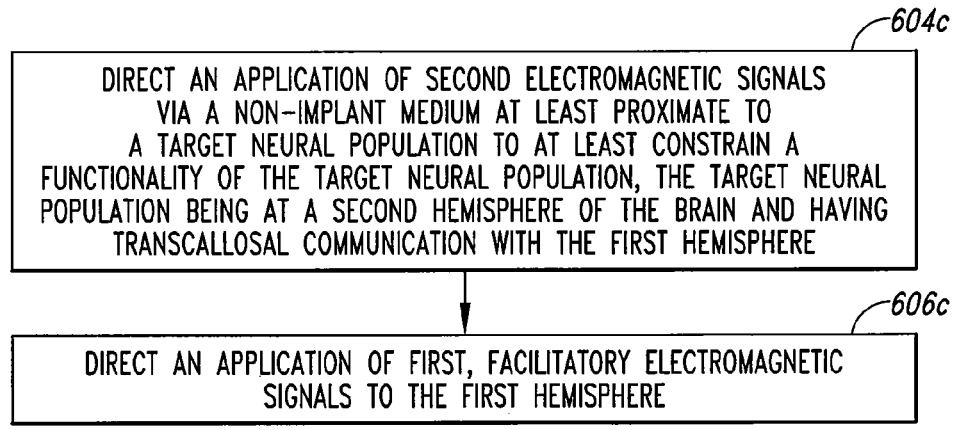
Figure 6D:
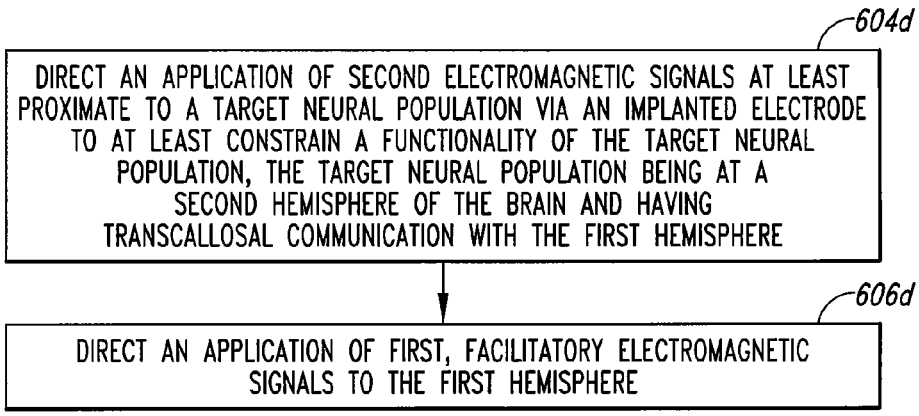
Figure 6E:
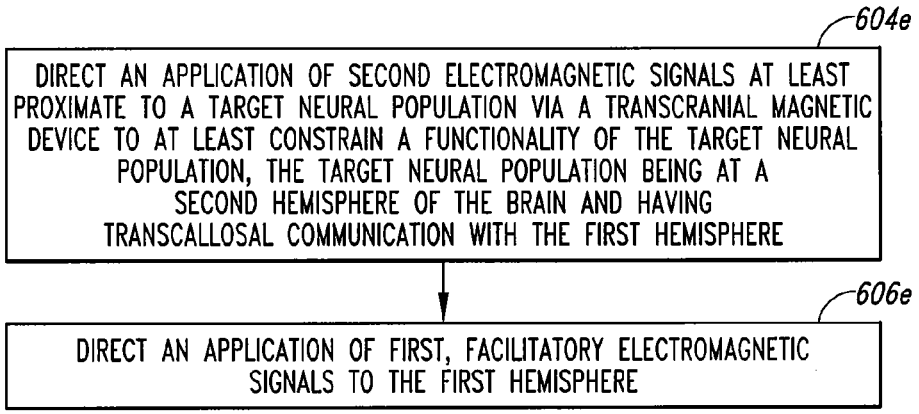
Figure 6F:
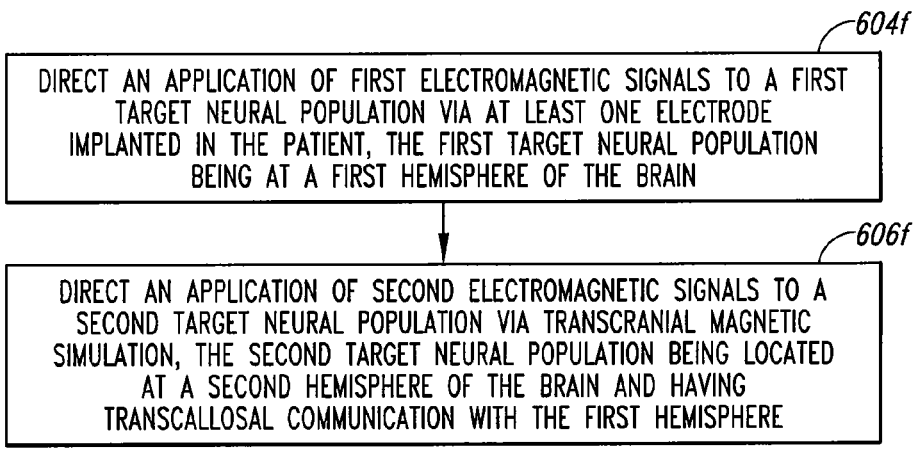
Figure 6G:
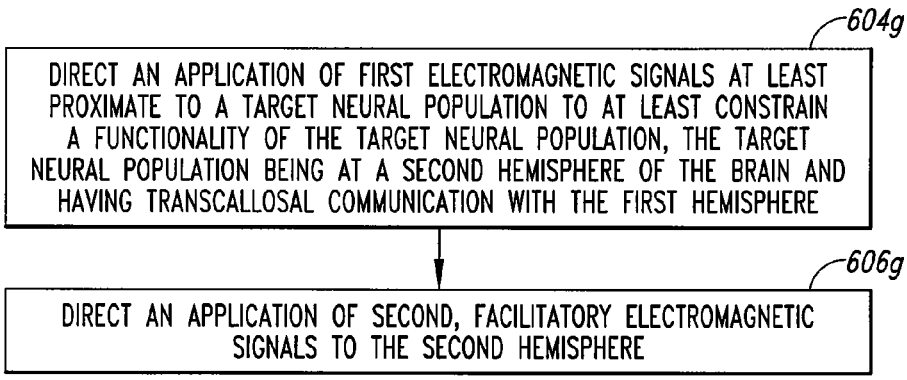
Figure 6H:
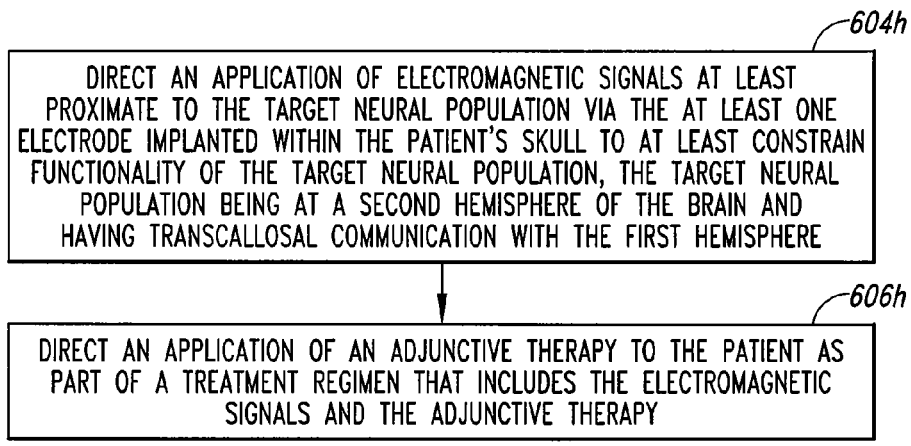
Figure 6I:
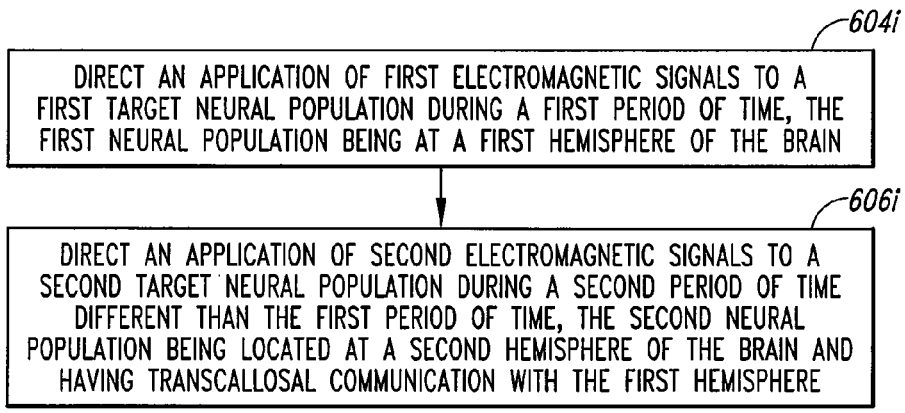
Figure 6J:
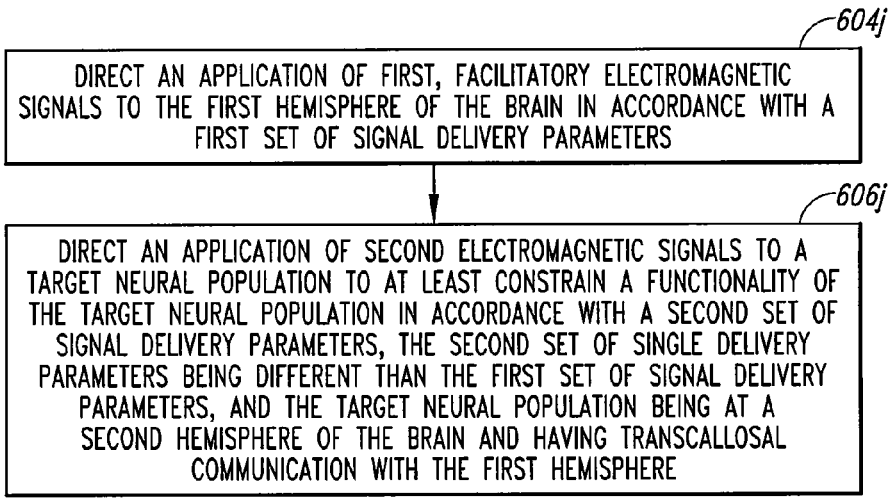
Figure 6K:
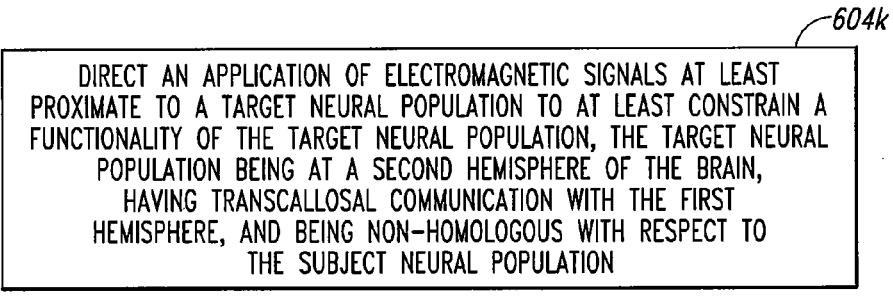
Figure 6L:
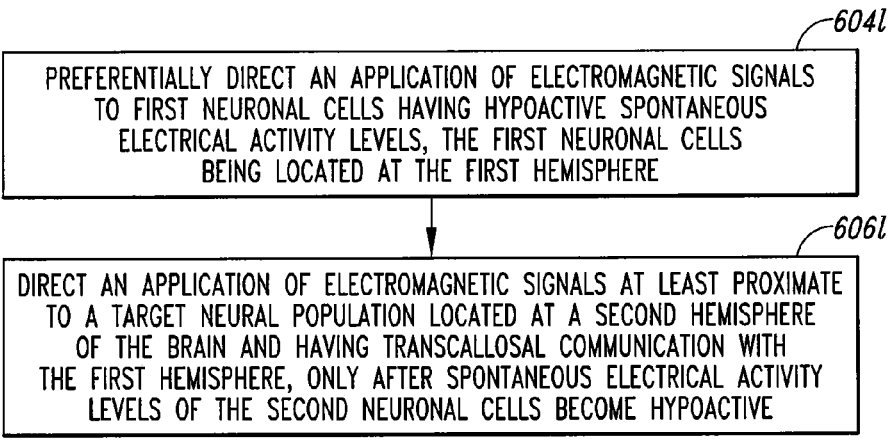
Figure 6M:
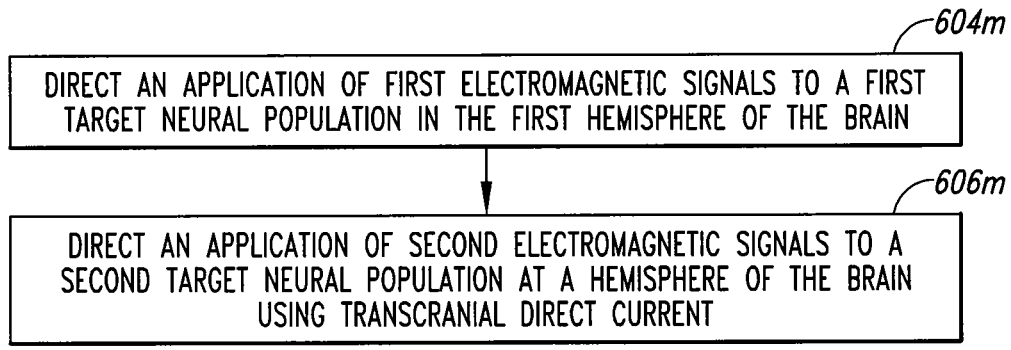
Figure 6N:
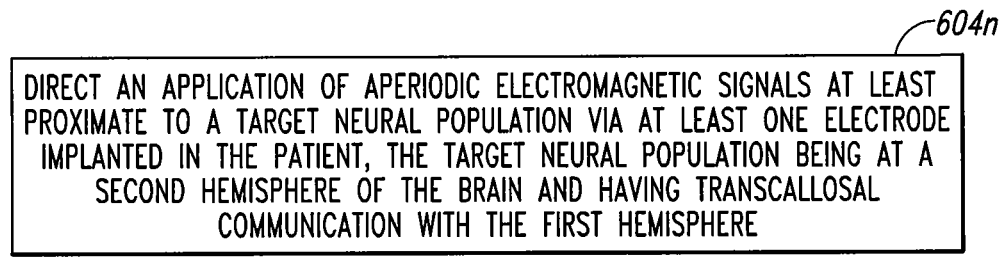

FIGS. 6A-6N are flow diagrams illustrating aspects of specific methods that were described generally above with reference to FIGS. 1-5. FIG. 6A illustrates a general method that includes identifying a patient as having a subject neural population at a first hemisphere of the patient's brain, wherein the subject neural population has (or had) or corresponds to a functionality that is capable of being improved (process portion 602). For example, the subject neural population can include an affected neural population having a functionality that is reduced or eliminated at least in part as a result of neurological damage to the brain. Process portion 602 can be performed by a neurologist or other qualified medical practitioner.

Process portion 604a includes providing therapy that includes directing signals to the second hemisphere of the patient's brain (e.g., the contralesional hemisphere). Accordingly, process portion 604a can be performed by a practitioner different than the practitioner performing process portion 602, and/or by instructions resident on a computer-readable medium. For example, aspects of the therapy provided in process portion 604a can be directed autonomously and/or semi-autonomously by a computer program in combination with an appropriate signal delivery device, with or without ongoing interaction by a human practitioner.

In several of the following embodiments, inhibitory signals are applied to the second hemisphere (e.g., the contralesional hemisphere). However, in at least some embodiments, inhibitory signals or signals that otherwise constrain the functionality of the target neural population need not be applied. In these cases, facilitatory signals can be provided to both hemispheres, at homologous and/or non-homologous neural structures. In at least some embodiments, the facilitatory signals can include theta burst signals, in only one hemisphere or in both hemispheres, depending upon factors including patient condition. It is believed that theta burst signals may particularly facilitate the patient's natural neuroplastic response. The signals can be applied to each hemisphere using the same modality or different modalities. For example, if the patient has an implanted electrode device at one hemisphere, another device (e.g., a TMS device or tDCS device) can be used on a periodic basis to provide additional signals to the other hemisphere, e.g., at less frequent intervals and/or for shorter time periods than are provided by the implanted device. The signals can be applied in accordance with different signal delivery parameters, depending on what type of structure the signals are directed to. For example, anodal signals may be directed to healthy neuronal tissue (e.g., at a contralesional target population) in combination with cathodal signals applied to a damaged subject neural population. This arrangement can facilitate the recovery of the subject neural population by facilitating the patient's natural neuroplastic response.

FIGS. 6B-6N illustrate specific processes and combinations of processes for providing the therapy identified in process portion 604a of FIG. 6A. In many instances, these processes are preceded by the step of identifying a patient as having an affected neural population (process portion 602, shown in FIG. 6A), but for purposes of illustration, this step is not shown in FIGS. 6B-6N.

Beginning with FIG. 6B, process portion 604b can include directing the application of electromagnetic signals at least proximate to a target neural population via at least one electrode implanted in the patient, to at least constrain a functionality of the target neural population. The target neural population is located at a second (e.g., contralesional) hemisphere of the brain, and may have transcallosal communication with the first hemisphere. The implanted electrode can be located at a cortical site of the brain, and/or at a subcortical or other site of the brain. Signals can be provided to one or more electrodes in accordance with a wide variety of signal delivery parameters.

FIG. 6C illustrates a process for delivering first and second electromagnetic signals. For purposes of illustration, the second signals are shown as being associated with the second (e.g., contralesional) hemisphere, and the first signals are shown as being associated with the first (ipsilesional) hemisphere. It will be understood that the first and second signals can be applied in any order and/or simultaneously depending upon the particular embodiment. Process portion 604c can include directing the application of second electromagnetic signals at least proximate to a target neural population at the second hemisphere, with the second electromagnetic signals provided via media other than an implanted electrode (e.g., via TMS or tDCS). Process portion 606c includes directing the application of first, facilitatory electromagnetic signals to the first hemisphere. For example, process portion 606c can include directing excitatory signals to or proximate to the subject neural population, and/or to other target neural populations located at the first (e.g., ipsilesional) hemisphere, so as to improve the overall neural functioning of the patient. Such signals can be delivered simultaneously with and/or sequential to the inhibitory signals applied to the target neural population at the second hemisphere.

FIGS. 6D and 6E illustrate further specific examples of the process shown in FIG. 6C. For example, FIG. 6D illustrates a process portion 604d in which the second electromagnetic signals are directed at least proximate to the (contralesional) target neural population via an implanted electrode. FIG. 6E illustrates a process portion 604e in which the second electromagnetic signals are provided via a transcranial magnetic device. In both instances, first, facilitatory electromagnetic signals can be provided to the first hemisphere, as indicated by process portions 606d and 606e, respectively.

FIG. 6F illustrates another process that includes directing electromagnetic signals via TMS. In particular, FIG. 6F illustrates a process portion 604f that includes directing the application of first electromagnetic signals to a first target neural population via at least one electrode implanted in the patient, and directing the application of second electromagnetic signals to a second target neural population at the second hemisphere via TMS (process portion 606f). A particular instance in which this embodiment may be utilized includes implanting an (ipsilesional) electrode or electrodes to apply facilitatory ipsilesional signals over a first period of time, and using TMS over a second, shorter period of time to inhibit the functionality of neuronal cells at the second hemisphere. Accordingly, the facilitatory stimulation at the first hemisphere may be provided by implanted electrodes for a period of days, weeks or months, in an autonomous or semi-autonomous fashion, and with reduced direct involvement by a practitioner, while the inhibitory signals can be provided via TMS directly by a practitioner over a shorter period of time e.g., during an office visit.

An embodiment of a process shown in FIG. 6G includes directing the application of first electromagnetic signals to at least constrain a functionality of the target neural population at the second hemisphere (process portion 604g) and directing the application of second, facilitatory electromagnetic signals, also to the second hemisphere (process portion 606g). For example, process portion 606g can include directing facilitatory signals to the target neural population after the target neural population has been inhibited for a period of time sufficient to allow functional recovery of neural populations at the first (e.g., ipsilesional) hemisphere.

In a process illustrated in FIG. 6H, the electromagnetic signals can be applied in association with an adjunctive therapy. Accordingly, process portion 604h can include directing the application of electromagnetic signals at least proximate to the target neural population (in the second or contralesional hemisphere) via an implanted electrode to constrain the functionality of the target neural population. In process portion 606h, the process can include directing the application of an adjunctive therapy to a patient as part of a treatment regimen that includes both the electromagnetic signals and the adjunctive therapy. The adjunctive therapy can have any of the characteristics described above with reference to FIG. 5, and can be engaged in simultaneously with, or temporally separate from, the application of electromagnetic signals, as part of an overall treatment regimen. In any of these embodiments, the administration of the adjunctive therapy can be coordinated with the administration of electromagnetic signals to enhance the patient's overall neural state.

FIG. 6I illustrates a process in accordance with which electromagnetic signals are provided to each of the brain hemispheres at different times. Accordingly, process portion 604i can include directing the application of first electromagnetic signals to a first target neural population (at the first hemisphere) during a first period of time. Process portion 606i can include directing the application of second electromagnetic signals to a second target neural population (at the second hemisphere) during a second period of time different than the first period of time. For example, the first electromagnetic signals can be applied while the patient engages in an adjunctive therapy, either under the direct supervision of a practitioner, or without direct practitioner supervision (e.g., when the adjunctive therapy includes ADL or a patient-directed therapy). In a further particular example, the first electromagnetic signals can be automatically triggered when the patient begins adjunctive therapy, and can be provided by one or more implanted electrodes. The stimulation can be automatically triggered when sensors associated with or placed on the patient detect the initiation of an adjunctive therapy activity, or when the patient initiates a computer-based routine (e.g., a computer-based routine that tests, evaluates, and/or exercises the patient's comprehension, language and/or memory functions). The manner in which signals are applied to the patient (e.g., the waveform, location and/or device via which the signals are applied) can differ during each time period. As was discussed generally above, the stimulation provided to each of the hemispheres can include a combination of inhibitory and/or facilitatory signals, depending upon the patient's particular condition.

FIG. 6J illustrates a process that includes applying electromagnetic signals in different manners depending upon whether the signals are applied ipsilesionally or contralesionally. For example, process portion 604j can include directing the application of first, facilitatory electromagnetic signals to the brain in accordance with a first set of signal delivery parameters, and process portion 606j can include directing the application of second electromagnetic signals to a target neural population to at least constrain a functionality of the target neural population in accordance with a second set of signal delivery parameters. The first set of signal delivery parameters can include a waveform selected or expected to produce neural facilitation or long term potentiation (LTP). For example, neural facilitation, LTP, or neural plasticity may result from the application of signals applied a) at frequencies above about 20 Hz, and in particular embodiments, at or above approximately 50 Hz, 80 Hz, or 100 Hz; b) at approximately 25%-75%, or about 50%, of a patient response level such as a movement or other type of threshold; and/or c) in a manner that preferentially shifts neural dendrites to a more depolarized or input-receptive state (e.g., via cathodal unipolar stimulation). The second electromagnetic signals can be delivered at lower frequencies (e.g., at frequencies of 0.1-20 Hz or, in particular embodiments, 1-10 Hz or 4-10 Hz) and possibly at other signal intensities, or in accordance with waveform parameters expected to result in long term depotentiation (LTD). In some embodiments, signals applied to both hemispheres are unipolar. In particular embodiments, signals applied to one hemisphere are anodal and signals applied to the other are cathodal. In other embodiments, signals applied to one hemisphere are unipolar and signals applied to the other are bipolar. In still further embodiments, signals applied to each hemisphere can be cycled or varied in different manners. The signals applied to each hemisphere can be applied sequentially in one embodiment, or simultaneously in another.

FIG. 6K illustrates a method that includes directing the application of electromagnetic signals to at least constrain a functionality of a target neural population that is non-homologous with respect to the subject neural population. For example, process portion 604k can include the application of electromagnetic signals in a manner generally similar to that described above with reference to FIG. 4.

FIG. 6L illustrates a method for varying the parameters in accordance with which signals are delivered, depending upon an activity level of the population to which the signals are directed. For example, process portion 604l can include preferentially directing electromagnetic signals to first neuronal cells located at the first hemisphere and having hypoactive spontaneous electrical activity levels. In process portion 606l, electromagnetic signals can be directed at least proximate to the target neural population located at the second hemisphere of the brain, possibly after spontaneous electrical activity levels of the second neuronal cells become normally active, less active, or hypoactive. Accordingly, an aspect of the method shown in FIG. 6L can include waiting for intrinsically hyperactive neuronal cells at the contralesional hemisphere to "settle down" before applying excitatory electromagnetic signals to those cells. Neural activity levels may be determined at one or more times in association with a functional imaging procedure (e.g., fMRI, PET, MEG, or NIRS), an electroencephalographic (EEG) procedure, a TMS procedure (e.g., in association with EMG during single or paired pulse measurements), or other procedure.

FIG. 6M illustrates a method that includes directing the application of first electromagnetic signals to a first target neural population in the first hemisphere of the brain, and directing the application of second electromagnetic signals to a second target neural population at the second hemisphere of the brain, using transcranial direct current (process portion 606m). The signals provided by tDCS can be provided so as to inhibit or facilitate the target neural population to which they are directed. For example, such signals can be directed in an anodal manner to facilitate the target neural population, and in a cathodal manner to inhibit the target neural population.

In still a further embodiment shown in FIG. 6N, a method of treatment can include directing the application of aperiodic electromagnetic signals via an implanted electrode at the second (e.g., contralesional) hemisphere of the brain (process portion 604n). The aperiodic electromagnetic signals can vary in accordance with several different arrangements, e.g., chaotically, randomly, and/or pseudorandomly.

Certain aspects of many of the foregoing embodiments may be combined in other embodiments. For example, in a particular embodiment, the practitioner can identify multiple pairs of signal delivery sites, with one site or sites in one hemisphere and the other site or sites in the other hemisphere, and then determine which pair is best suited to producing the desired result. In some cases, the desired result includes improved patient performance and/or recovery, and in other cases, the desired result can include identifying which site pair produces a desired patient response with the lowest power input from a signal delivery device. For example, using TMS or tDCS, the practitioner can apply signals to both hemispheres in accordance with a wide variety of combinations, e.g., facilitatory in one hemisphere, inhibitory in the other; anodal in one hemisphere, cathodal in the other; at a given cortical location in one hemisphere, and a non-homologous location in the other. With each combination, the practitioner can identify the signal parameters (e.g., intensity level) that triggers a desired patient response (e.g., motor threshold or another measure). Based on the results, the practitioner can select the site pair or pairs that produce the desired response with the lowest intensity signal input. The practitioner can then implant electrodes at both hemispheres relative to the selected site pair or pairs, and apply signals (e.g., subthreshold signals, for example, at about 25%-75%, or approximately 50%, of a patient response threshold such as a movement threshold) with a reduced power consumption and/or expectation of enhanced therapeutic efficacy than if the foregoing testing had not been conducted.

D. Further Systems for Applying Electromagnetic Signals

Figure 7:
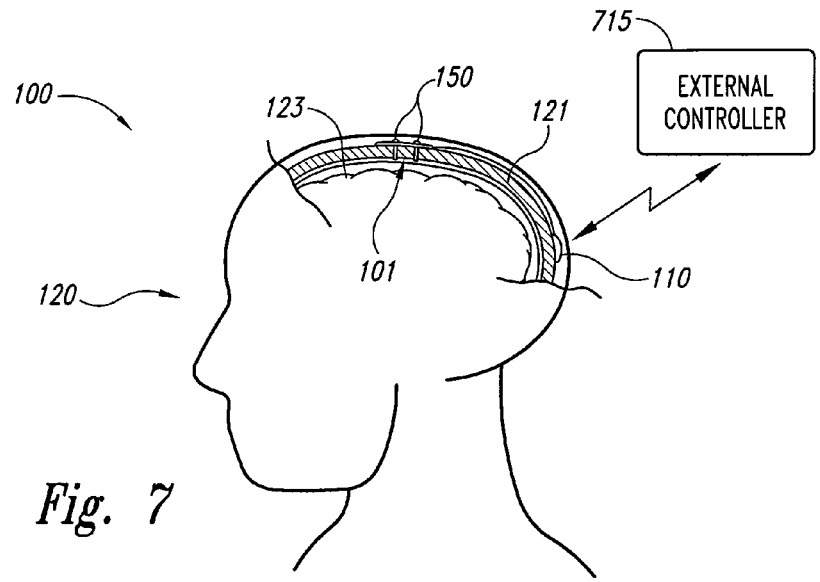
FIG. 7 illustrates an electrode device operatively coupled to an external controller in accordance with another embodiment of the invention.

Many aspects of the methods described above can be performed by systems similar to that described above with reference to FIG. 1. In other embodiments, systems having similar and/or different capabilities can perform similar and/or different functions. For example, the system 100 shown in FIG. 1 can include a pulse system 110 that is implanted at a subclavicular location. The pulse system 110 can also be controlled internally via pre-programmed instructions that allow the pulse system 110 to operate autonomously after implantation. In other embodiments, the pulse system 110 can be implanted at other locations, and at least some aspects of the pulse system 110 can be controlled externally. For example, FIG. 7 illustrates an embodiment of the system 100 in which the pulse system 110 is positioned on the external surface of the skull 121, beneath the scalp. The pulse system 110 can be controlled internally and/or via an external controller 715.

Figure 8:
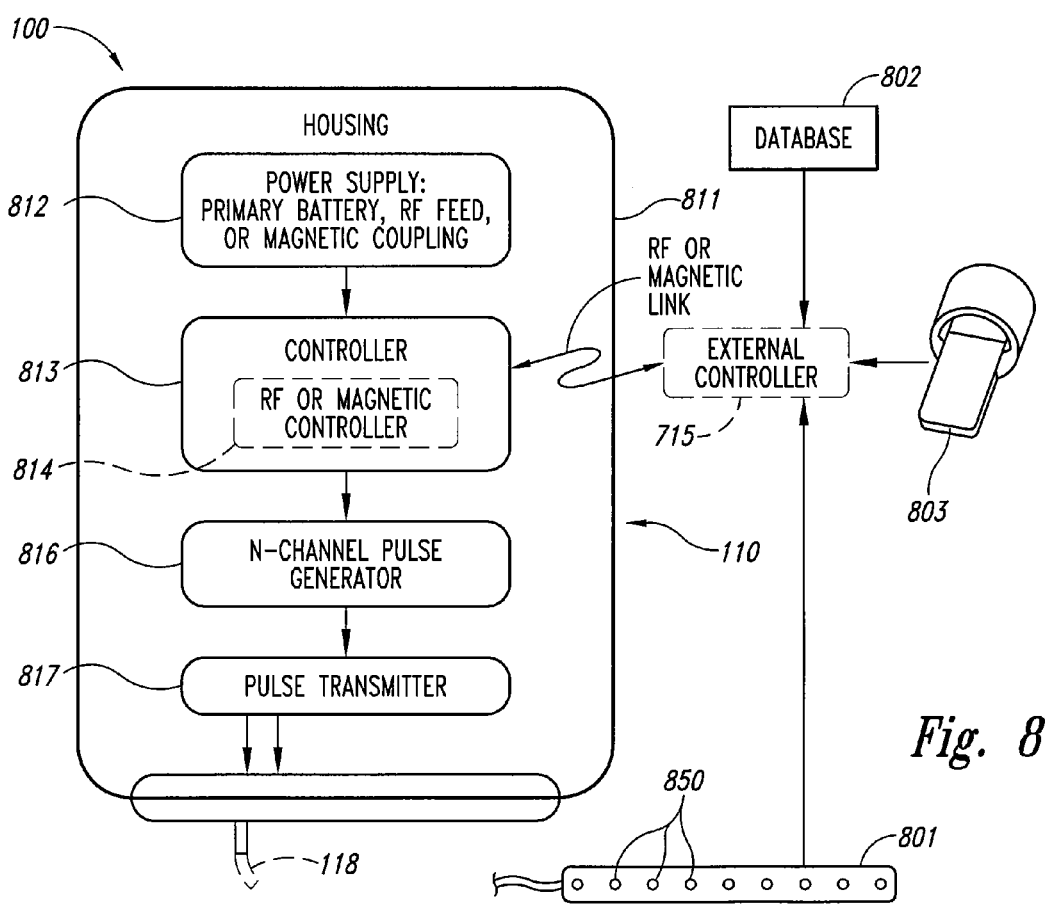
FIG. 8 is a schematic illustration of a pulse system configured in accordance with several embodiments of the invention.

FIG. 8 schematically illustrates one pulse system 110 suitable for use in the system 100 described above. The pulse system 110 generally includes a housing 811 carrying a power supply 812, an integrated controller 813, a pulse generator 816, and a pulse transmitter 817. In certain embodiments, a portion of the housing 811 may comprise a signal return electrode. The power supply 812 can be a primary battery, such as a rechargeable battery or other suitable device for storing electrical energy. In other embodiments, the power supply 812 can be an RF transducer or a magnetic transducer that receives broadcast energy emitted from an external power source and that converts the broadcast energy into power for the electrical components of the pulse system 110.

In one embodiment, the integrated controller 813 can include a processor, a memory, and/or a programmable computer medium. The integrated controller 813, for example, can be a microcomputer, and the programmable computer medium can include software loaded into the memory of the computer, and/or hardware that performs the requisite control functions. In another embodiment identified by dashed lines in FIG. 8, the integrated controller 813 can include an integrated RF or magnetic controller 814 that communicates with the external controller 715 via an RF or magnetic link. In such an embodiment, many of the functions performed by the integrated controller 813 may be resident on the external controller 715 and the integrated portion 814 of the integrated controller 813 may include a wireless communication system.

The integrated controller 813 is operatively coupled to, and provides control signals to, the pulse generator 816, which may include a plurality of channels that send appropriate electrical pulses to the pulse transmitter 817. The pulse transmitter 817 is coupled to electrodes 850 carried by an electrode device 801. In one embodiment, each of these electrodes 850 is configured to be physically connected to a separate lead, allowing each electrode 850 to communicate with the pulse generator 816 via a dedicated channel. Accordingly, the pulse generator 816 may have multiple channels, with at least one channel associated with each of the electrodes 850 described above. Suitable components for the power supply 812, the integrated controller 813, the external controller 715, the pulse generator 816, and the pulse transmitter 817 are known to persons skilled in the art of implantable medical devices.

The pulse system 110 can be programmed and operated to adjust a wide variety of stimulation parameters, for example, which electrodes are active and inactive, whether electrical stimulation is provided in a unipolar or bipolar manner, and/or how stimulation signals are varied (e.g., at frequencies expected to produce inhibitory or facilitatory effects). In particular embodiments, the pulse system 110 can be used to control the polarity, frequency, duty cycle, amplitude, and/or spatial and/or topographical qualities of the stimulation. The stimulation can be varied to match naturally occurring burst patterns (e.g., theta-burst and/or other types of burst stimulation), and/or the stimulation can be varied in a predetermined, pseudorandom, and/or other aperiodic manner at one or more times and/or locations.

In particular embodiments, the pulse system 110 can receive information from selected sources, with the information being provided to influence the time and/or manner by which the signal delivery parameters are varied. For example, the pulse system 110 can communicate with a database 802 that stores values identifying when stimulation parameters should be changed. In a particular aspect of this embodiment, the database 802 can include information identifying how much time should be spent delivering inhibitory signals to the target neural population, before applying facilitatory signals to that population. In other embodiments, the decision to change stimulation parameters can be made on a patient-by-patient basis. For example, in a particular embodiment, particular electrodes 850 may deliver electromagnetic signals to the patient and/or receive electromagnetic signals from the patient that are indicative of the level of functioning of one or more neural populations. Accordingly, information received from the electrode device 801 can be used to determine the effectiveness of a given set of signal parameters and, based upon this information, can be used to update the signal delivery parameters.

In other embodiments, other techniques can be used to provide patient-specific feedback. For example, a magnetic resonance chamber 803 can provide information corresponding to the locations at which a particular type of brain activity is occurring and/or the level of functioning at these locations, and can be used to identify additional locations and/or additional parameters in accordance with which electrical signals can be provided to the patient to further increase functionality. Accordingly, the system 100 can include a direction component configured to direct a change in an electromagnetic signal applied to the patient's brain based at least in part on an indication received from one or more sources. These sources can include a detection component (e.g., the electrode device 101 and/or the magnetic resonance chamber 803) or a timing component (e.g., the database 802). In either case, one of the changes directed by the direction component can be a change from an inhibitory signal to a facilitatory signal.

E. Further Examples of Electrode Devices

Figure 9:
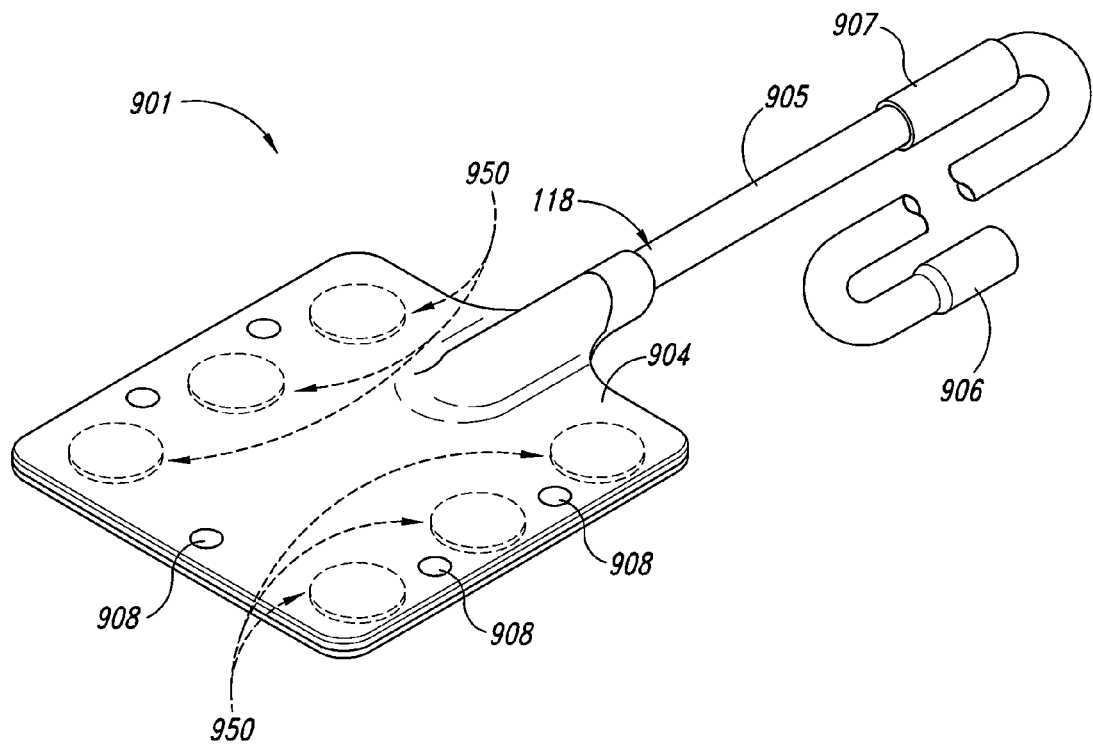
FIG. 9 is an isometric view of an electrode device that carries electrodes in accordance with an embodiment of the invention.

FIG. 9 is a top, partially hidden isometric view of an embodiment of an electrode device 901 described above, configured to carry multiple cortical electrodes 950. The electrodes 950 can be carried by a flexible support member 904 to place each electrode 950 in contact with a stimulation site of the patient when the support member 904 is implanted. Electrical signals can be transmitted to the electrodes 950 via leads carried in the communication link 118. The communication link 118 can include a cable 905 that is connected to the pulse system 110 (FIG. 8) via a connector 906, and is protected with a protective sleeve 907. Coupling apertures or holes 908 can facilitate temporary attachment of the electrode device 901 to the dura mater at, or at least proximate to, a stimulation site. The electrodes 950 can be biased cathodally and/or anodally. In an embodiment shown in FIG. 9, the electrode device 901 can include six electrodes 950 arranged in a 2×3 electrode array (i.e., two rows of three electrodes each), and in other embodiments, the electrode device 901 can include more or fewer electrodes 950 arranged in symmetrical or asymmetrical arrays. The particular arrangement of the electrodes 950 can be selected based on the region of the patient's brain that is to be stimulated, and/or the patient's condition.

Figure 10:
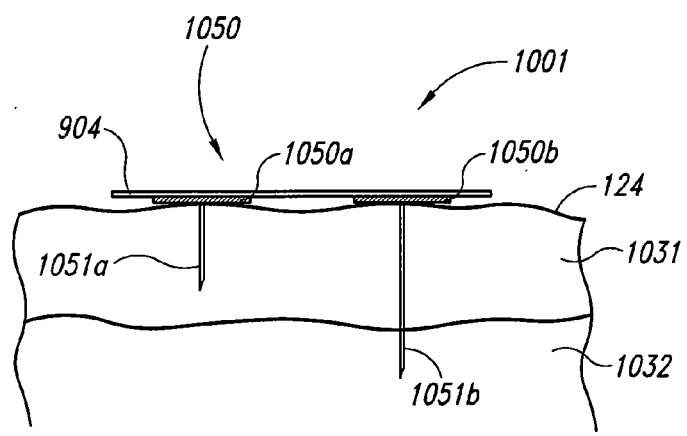
FIG. 10 illustrates an electrode device having electrodes configured to deliver electromagnetic signals to cortical and subcortical regions in accordance with an embodiment of the invention.

FIG. 10 is a side elevational view of an electrode device 1001 configured to stimulate cortical and/or subcortical tissue in accordance with another embodiment of the invention. The electrode device 1001 includes multiple electrodes 1050, two of which are shown in FIG. 10 as a first electrode 1050a and a second electrode 1050b. The electrodes 1050 also include first and second electrically conductive pins 1051a and 1051b. The pins 1051a, 1051b can be configured to extend below the pial surface of the cortex 1031. For example, because the length of the first pin 1051a is less than the thickness of the cortex 1031, the tip of the first pin 1051a will accordingly conduct the electrical pulses to a stimulation site within the cortex 1031 below the pial surface.

The length of the second pin 1051b is greater than the thickness of the cortex 1031 to conduct the electrical pulses to a portion of the brain below the cortex 1031, e.g., the subcortex 1032. The lengths of both pins can be selected to conduct the electrical pulses to stimulation sites below the pia mater 124. As such, the lengths of the pins 1051a, 1051b can be the same for each electrode 1050 or different for individual electrodes 1050. Additionally, only a selected portion of the electrodes 1050 and the pins 1051 can have an exposed conductive area. For example, the electrode 1050 and a portion of the pins 1051 can be covered with a dielectric material so that the only exposed conductive material is at the tips of the pins 1051. It will be appreciated that any of the electrode configurations described above can apply an electrical current to stimulation sites below the pia mater 124 by providing pin-like electrodes in a manner similar to that shown in FIG. 9A.

Figure 11:
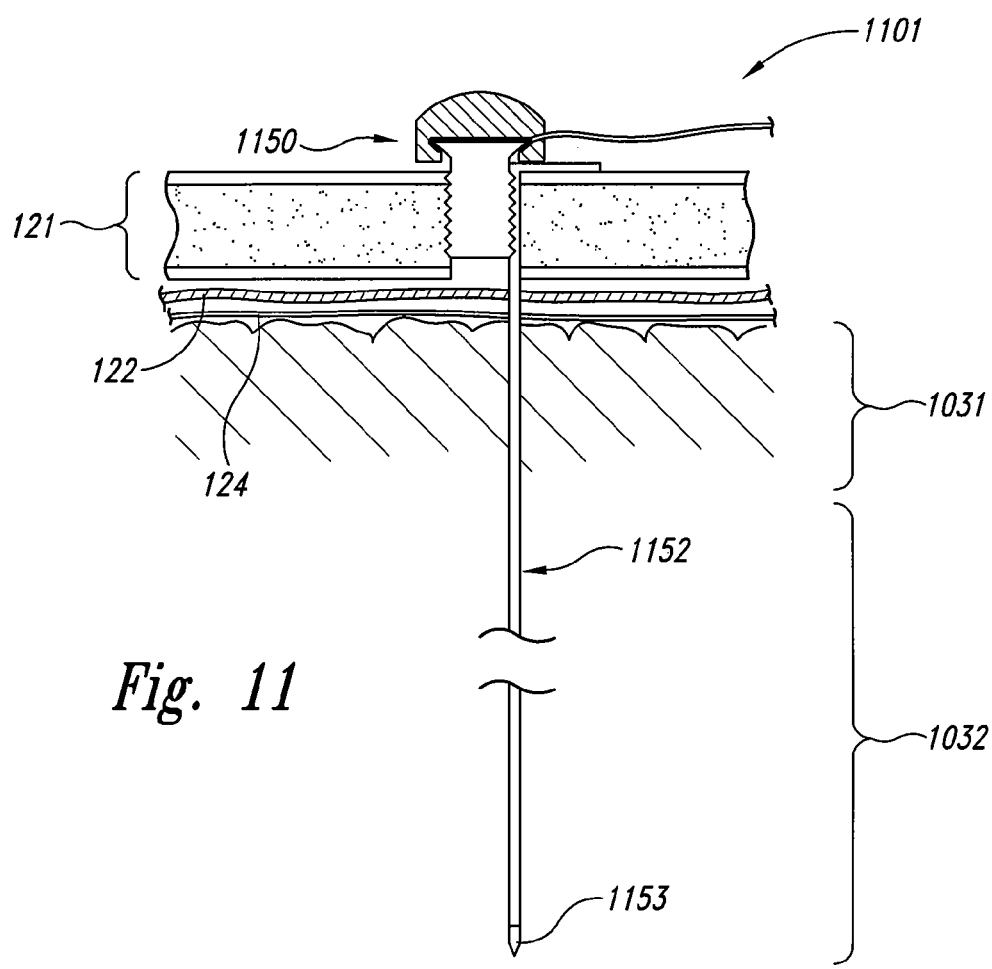
FIG. 11 is a side elevation view of an electrode configured to deliver electromagnetic signals to a subcortical region in accordance with an embodiment of the invention.

FIG. 11 illustrates an electrode device 1101 that may be configured to apply electrical stimulation signals to the cortical region 1031 or the subcortical region 1032 in accordance with another embodiment of the invention. The electrode device 1101 can include an electrode 1150 having a head and a threaded shaft that extends through a pilot hole in the patient's skull 121. If the electrode 1150 is intended for cortical stimulation, it can extend through the skull 121 to contact the dura mater 122 or the pia mater 124. If the electrode 1154 is to be used for subcortical stimulation, it can include an elongate conductive member 1152 that extends downwardly through the cortical region 1031 into the subcortical region 1032. Most of the length of the elongate conductive member can be insulated, with just a tip 1153 exposed to provide electrical stimulation in only the subcortical region 1032. Further details of electrode devices that may be suitable for electromagnetic stimulation in accordance with other embodiments of the invention are described in the following pending U.S. Applications/issued patents, all of which are incorporated herein by reference: 2005/0075680-A1; 2004/0102828-A1; and U.S. Pat. No. 7,010,351.

Figure 12:
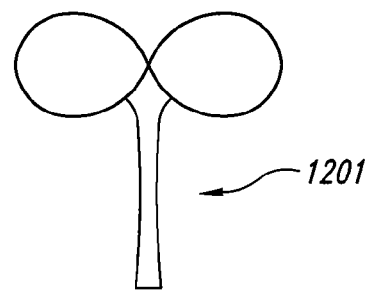
FIG. 12 is a schematic illustration of a transcranial magnetic stimulation device for treating a patient in accordance with still further embodiments of the invention.

In many of the embodiments described above, the electromagnetic signals delivered to the patient include signals delivered when an electrical current passes through an electrode positioned at least proximate to the target neural population. In such instances, at least a portion of the electrode is typically positioned within the patient's skull to improve the efficiency with which electrical signals are provided to the patient, and to reduce the power required to deliver such signals. In other embodiments, such signals can include magnetic signals delivered from external to the patient. Accordingly, as shown in FIG. 12, a device 1201 in accordance with another embodiment of the invention can include a magnetic coil or other suitable magnetic device configured to provide transcranial magnetic stimulation (TMS) to the patient. In other embodiments, other techniques and/or devices can be used to provide suitable electromagnetic stimulation. For example, signals can be delivered through the patient's skull via transcranial direct current stimulators.

From the foregoing, it will be appreciated that specific embodiments of the invention have been described herein for purposes of illustration, but that various modifications may be made without deviating from the invention. For example, certain aspects of the methods described above may be automated or partially automated, and may be implemented on computer systems and/or via computer-readable media. Aspects of the invention described in the context of particular embodiments may be combined or eliminated in other embodiments. For example, the pulse controller described with reference to FIG. 8 can be coupled to any of the electrode devices described in connection with other Figures of the application. Aspects of the invention described in the context of an ipsilesional right hemisphere and a contralesional left hemisphere can be applied in generally the same manner to an ipsilesional left hemisphere and a contralesional right hemisphere. As was also described above, many if not all these foregoing techniques can be applied to increase the functionality of the brain of a patient who has not suffered a lesion or other damage, and whose brain functioning is at normal or even above normal levels. Although advantages associated with certain embodiments of the invention have been described in the context of those embodiments, other embodiments may also exhibit such advantages. Additionally, none of the foregoing embodiments need necessarily exhibit such advantages to fall within the scope of the invention. Accordingly, the invention is not limited except as by the appended claims.

We claim:

1. A method for treating a patient having a subject neural population in a first hemisphere of the patient's brain, wherein the subject neural population has or had a functionality that is capable of being improved, the method comprising:

identifying an ipsilesional target neural population on a first hemisphere;

identifying a contralesional target neural population on a second hemisphere having transcallosal communication with the first hemisphere;

facilitating functionality of the ipsilesional neural population by directing an application of first, facilitatory electromagnetic signals to the ipsilesional neural population of the first hemisphere such that the facilitatory signals are cathodal signals having a frequency of 50 Hz to 100 Hz; and constraining functionality of the contralesional neural population by directing an application of second electromagnetic signals to inhibit, disrupt or depotentiate the contralesional target neural population via a transcranial magnetic device and the second signals are anodal signals having a frequency of 1 Hz to 10 Hz thereby improving functionality of the patient.

2. The method of claim 1 wherein directing the application of the second electromagnetic signals includes directing the application of electromagnetic signals at a frequency of from 4 Hz to 10 Hz.

3. A method for treating a patient having a subject neural population in a first hemisphere of the patient's brain, wherein the subject neural population has or had a functionality that is capable of being improved, the method comprising:

identifying an ipsilesional target neural population on a first hemisphere;

identifying a contralesional target neural population on a second hemisphere having transcallosal communication with the first hemisphere;

facilitating functionality of the ipsilesional neural population by directing an application of first, facilitatory electromagnetic signals to the first hemisphere such that the first signals are cathodal signals having a frequency of 50 Hz to 100 Hz; and constraining functionality of the contralesional target neural population by directing an application of second electromagnetic signals to the contralesional target neural population to at least constrain a functionality of the target neural population such that the second signals are anodal signals having a frequency of 1 Hz to 10 Hz and thereby improving functionality of the patient.

4. The method of claim 3 wherein directing the application of the second electromagnetic signals includes directing the application of electromagnetic signals to inhibit the contralesional target neural population.

5. The method of claim 3 wherein directing the application of the second electromagnetic signals includes directing the application of electromagnetic signals to depotentiate the contralesional target neural population.

6. The method of claim 3 wherein directing the application of the second electromagnetic signals includes directing the application of electromagnetic signals at a frequency of from 4 Hz to 10 Hz.

7. The method of claim 3 wherein directing the application of the second electromagnetic signals includes directing the application of electromagnetic signals at a sub-threshold level for the target neural population.

8. The method of claim 3 wherein directing the application of the second electromagnetic signals includes directing the application of electromagnetic signals via an electrode implanted within the patient's skull.

9. The method of claim 3 wherein directing the application of the first, the second, or both the first and the second electromagnetic signals includes directing the application of electromagnetic signals via a transcranial magnetic device.

10. The method of claim 3 wherein directing the application of the first, the second, or both the first and the second electromagnetic signals includes directing the application of electromagnetic signals via a one or more electrodes implanted within the patient's skull.

11. The method of claim 3 wherein directing the application of facilitatory electromagnetic signals includes directing the application of excitatory signals.

12. The method of claim 3 wherein directing the application of the second electromagnetic signals includes directing the application of the second electromagnetic signals to a contralesional target neural population that is homologous to the subject neural population.

13. The method of claim 3 wherein directing the application of the second electromagnetic signals includes directing the application of the second electromagnetic signals to a target neural population that is homologous to the subject neural population, and wherein the method further comprises directing the application of facilitatory signals to a non-homologous neural population at the second hemisphere.

14. The method of claim 3 wherein directing the application of the second electromagnetic signals includes directing the application of the second electromagnetic signals to a target neural population that is non-homologous to the subject neural population, and wherein the method further comprises directing the application of facilitatory signals to a homologous neural population at the second hemisphere.

15. The method of claim 3 wherein directing the application of the second electromagnetic signals includes directing the application of the second electromagnetic signals to a target neural population that is not homologous to the subject neural population.

16. The method of claim 3 wherein directing the application of the second electromagnetic signals includes directing the application of the second electromagnetic signals to a target neural population that is not homologous to the subject neural population, and has more transcallosal connections than does a neural population that is homologous to the subject neural population.

17. The method of claim 16 wherein directing the application of the second electromagnetic signals includes directing the application of the second electromagnetic signals to the contralesional premotor cortex.

18. The method of claim 3, further comprising directing additional facilitatory electromagnetic signals at least proximate to the target neural population.

19. The method of claim 3, further comprising directing additional facilitatory electromagnetic signals at least proximate to the target neural population after directing the application of inhibitory electromagnetic signals at least proximate to the target neural population.

20. The method of claim 3 wherein directing the application of the second electromagnetic signals to the target neural population includes directing the application of the second electromagnetic signals for a target period of time associated with an expected improvement in functionality of neurons at the first hemisphere, and wherein the method further comprises directing additional facilitatory electromagnetic signals to the target neural population after the target period of time has elapsed.

21. The method of claim 3, further comprising:
  detecting an improvement in functionality of neurons at the first hemisphere; and
  after detecting an improvement in functionality of the neurons at the first hemisphere, directing additional, facilitatory electromagnetic signals to the target neural population.

22. The method of claim 3 wherein directing the application of the first electromagnetic signals to the first hemisphere includes directing the application of the first electromagnetic signals simultaneously with directing the application of the second electromagnetic signals to the target neural population, and wherein the method further comprises:
  detecting an improvement in functionality of neurons at the first hemisphere; and
  after detecting an improvement in functionality of neurons at the first hemisphere, directing additional, facilitatory electromagnetic signals to the target neural population.

23. The method of claim 3, further comprising directing the patient to undergo adjunctive therapy as part of a treatment regimen that also includes the application of the first and the second electromagnetic signals.

24. The method of claim 3, further comprising:
  directing the patient to undergo adjunctive therapy as part of a treatment regimen that also includes the application of the first and the second electromagnetic signals; and
  selecting a characteristic of at least one of the first and the second electromagnetic signals based at least in part on a characteristic of the adjunctive therapy, or selecting a characteristic of the adjunctive therapy based at least in part on a characteristic of at least one of the first and the second electromagnetic signals, or both.

25. The method of claim 3, further comprising identifying the patient as having a subject neural population affected by a stroke.

26. The method of claim 3, further comprising identifying the patient as having a subject neural population affected by a neurological disease.

27. The method of claim 3, further comprising identifying the patient as having a subject neural population affected by a lesion.

28. The method of claim 3 wherein directing the application of electromagnetic signals is performed by computer-based instructions.

* * * * *